US011559640B2

(12) United States Patent
Haruta et al.

(10) Patent No.: US 11,559,640 B2
(45) Date of Patent: Jan. 24, 2023

(54) MEDICINE STORAGE CARTRIDGE WITH NOZZLE, SPRAYER THEREFOR, AND POWDERED MEDICINE DISPENSING DEVICE FOR NASAL CAVITY

(71) Applicant: Shin Nippon Biomedical Laboratories, Ltd., Kagoshima (JP)

(72) Inventors: Shunji Haruta, Kagoshima (JP); Genji Satoyoshi, Kagoshima (JP); Hideaki Mishima, Kagoshima (JP)

(73) Assignee: Shin Nippon Biomedical Laboratories, Ltd., Kagoshima (JP)

( * ) Notice: Subject to any disclaimer, the term of this patent is extended or adjusted under 35 U.S.C. 154(b) by 319 days.

(21) Appl. No.: 16/647,475

(22) PCT Filed: Aug. 17, 2018

(86) PCT No.: PCT/JP2018/030477
§ 371 (c)(1),
(2) Date: Mar. 13, 2020

(87) PCT Pub. No.: WO2019/054121
PCT Pub. Date: Mar. 21, 2019

(65) Prior Publication Data

US 2020/0276402 A1 Sep. 3, 2020

(30) Foreign Application Priority Data

Sep. 15, 2017 (JP) ............................ JP2017-177261

(51) Int. Cl.
*A61M 15/08* (2006.01)
*A61M 15/00* (2006.01)
*A61M 11/02* (2006.01)

(52) U.S. Cl.
CPC ............ *A61M 15/08* (2013.01); *A61M 11/02* (2013.01); *A61M 15/0043* (2014.02);
(Continued)

(58) Field of Classification Search
CPC .. A61M 11/00–003; A61M 11/006–02; A61M 11/06; A61M 15/00–0001;
(Continued)

(56) References Cited

U.S. PATENT DOCUMENTS 4,017,007 A 4/1977 Riccio
5,328,099 A 7/1994 Petit et al.
(Continued)

FOREIGN PATENT DOCUMENTS

CH 518744 A1 2/1972
EP 1721628 A1 11/2006
(Continued)

OTHER PUBLICATIONS

International Search Report from the Japanese Patent Office for International Application No. PCT/JP2018/030477 dated Sep. 18, 2018.

(Continued)

*Primary Examiner* — Rachel T Sippel
(74) *Attorney, Agent, or Firm* — Finnegan, Henderson, Farabow, Garrett & Dunner, LLP

(57) ABSTRACT

A nozzled cartridge (20) for storing medicine, according to an aspect of the present application, includes a medicine container (21) that is to be filled with a predetermined quantity of a powdered medicine, a nozzle portion (22) that is formed on the medicine container (21) and that ejects the powdered medicine, a closing member (24) that closes an opening (**22*a*) in the nozzle portion (22), and a valve member (25) that functions as a plug to close another opening (23*a*) in the medicine container (21), and that is opened when administering medicine. The nozzled cartridge (20) is detachably mountable to a sprayer (30**) when administering medicine.

16 Claims, 15 Drawing Sheets

(52) U.S. Cl.
CPC ... *A61M 15/0061* (2014.02); *A61M 2202/064* (2013.01); *A61M 2205/073* (2013.01)

(58) Field of Classification Search
CPC .......... A61M 15/0028; A61M 15/0043; A61M 15/0061; A61M 15/09; A61M 15/08
See application file for complete search history.

(56) References Cited

U.S. PATENT DOCUMENTS

| | | | |
|---|---|---|---|
| 5,683,361 | A | 11/1997 | Elk et al. |
| 6,398,074 | B1 | 6/2002 | Bruna et al. |
| 2003/0178440 | A1 | 9/2003 | Wright |
| 2004/0050885 | A1 | 3/2004 | Stradella |
| 2005/0177095 | A1 | 8/2005 | Tsutsui |
| 2006/0254585 | A1 | 11/2006 | Ishizeki et al. |
| 2009/0166379 | A1 | 7/2009 | Wright et al. |
| 2011/0045088 | A1 | 2/2011 | Tsutsui et al. |
| 2012/0103332 | A1 | 5/2012 | Parsons |
| 2013/0158474 | A1 | 6/2013 | Sullivan et al. |
| 2014/0060535 | A1 | 3/2014 | Tsutsui |
| 2016/0129205 | A1 | 5/2016 | Shahaf et al. |
| 2016/0296957 | A1 | 10/2016 | Baillet et al. |

FOREIGN PATENT DOCUMENTS

| | | | | |
|---|---|---|---|---|
| JP | S59-034267 | A | 2/1984 | |
| JP | 2002-505981 | A | 2/2002 | |
| JP | 2004-532717 | A | 10/2004 | |
| JP | 2011-15954 | * | 1/2011 | ............ A61M 13/00 |
| JP | 2011-015954 | A | 1/2011 | |
| JP | 2016-140527 | A1 | 8/2016 | |
| JP | 2016-523647 | A | 8/2016 | |
| WO | WO2001/095962 | | 12/2001 | |
| WO | WO-2003/095008 | | 11/2003 | |
| WO | WO-2006/030210 | | 3/2006 | |
| WO | WO-2012/105236 | | 8/2012 | |
| WO | WO-2012/119153 | | 9/2012 | |
| WO | WO-2012/154859 | | 11/2012 | |
| WO | WO-2013/128447 | | 9/2013 | |
| WO | WO-2014/179228 | | 11/2014 | |
| WO | WO-2015/025324 | | 2/2015 | |
| WO | WO-2017/044897 | | 3/2017 | |

OTHER PUBLICATIONS

Concise explanation of relevance, under 37 C.F.R. § 1.98(a)(3)(i), of JP-S59-034267.

* cited by examiner

MEDICINE STORAGE CARTRIDGE WITH NOZZLE, SPRAYER THEREFOR, AND POWDERED MEDICINE DISPENSING DEVICE FOR NASAL CAVITY

This application is a national stage filing under 35 U.S.C. § 371 of International Application No. PCT/JP2018/030477, filed on Aug. 17, 2018, and published as WO/2019/054121, which claims priority of Japanese Patent Application No. 2017-177261, filed on Sep. 15, 2017. International Application No. PCT/JP2018/030477 is incorporated herein by reference in its entirety.

TECHNICAL FIELD

The present invention relates to a nozzled cartridge for storing medicine, a sprayer therefor, and a powdered medicine dispensing device for nasal cavities.

BACKGROUND ART

There is a generally known treatment method where powdered medicine is dispensed in the nasal cavities of a patient who has a disorder such as rhinitis, nasal allergy, or the like. In this treatment method, powdered medicine with which a capsule is filled is dispensed in the nasal cavities using a dedicated dispensing device. Also, medicine dispensing devices used for this treatment method have conventionally been proposed (see Patent Document 1, for example).

In the dispensing device described in Patent Document 1, a pump unit is provided on an air inflow side of a cylindrical member, a recessed portion where a capsule is inserted is formed at an air outflow side of this cylindrical member, a capsule accommodating portion is formed by fitting a tip portion to this recessed portion, and an air induction channel having a valve mechanism is formed from this capsule accommodating portion toward the pump unit. Another valve mechanism is provided at the other side of the pump unit, so that air is supplied to the capsule accommodating portion via the air induction channel when pressing the pump unit, and air is externally suctioned into the pump unit when the pump unit returns, by this valve mechanism and the valve mechanism in the air induction channel. Further, the dispensing device has a cap that fits to the tip portion of the cylindrical member, and a needle extending in the axial direction is provided on the inner side of this cap. The configuration thereof is such that both sides of the capsule in the axial direction are perforated by putting the cap on in a state where the recessed portion of the cylindrical member and the tip portion having an opening are fit to each other.

First, perforation of the capsule by the device configured thus is performed by inserting the capsule filled with powdered medicine in the recessed portion of the cylindrical member, following which the tip portion is fitted and the capsule is attached by insertion into the capsule accommodating portion, and the cap is put on to the tip portion made of hard resin, whereby both tip portions of the capsule in the axial direction are perforated by the needle provided on the inner side of the cap, which is guided to the tip portion.

Next, in order to administer the medicine, the cap is removed from the cylindrical member and user inserts the tip portion into one nostril. The pump unit is then pressed, whereby air from the pump unit flows into the capsule via the air induction channel, and medicine inside the capsule is dispensed by being delivered to inside the nasal cavity of the user. Dispensing medicine to both nasal cavities is performed by repeating the actions from inserting the tip portion and thereafter, thereby dispensing medicine to both nasal cavities.

CITATION LIST

Patent Document

Patent Document 1: Patent Publication JP-A-S59-34267

SUMMARY

Technical Problem

However, practically none of the conventional medicine dispensing devices for nasal administration have been improved from the perspective of (a) improved uniformity of amount administered in each dose, (b) improved drug preservability of preservation container, (c) facilitating ease-of-use regarding administration operations, and (d) improved portability.

That is to say, medicine dispensing devices for nasal administration of powdered medicine include (i) multi-dose administering devices where medicine for multiple doses is collectively stored in a container within the administering device, and one dose of medicine is measured out from the container and administered, each time administration is performed (see WO 2001/095962, for example), and (ii) single-dose administering devices where a container such as a capsule, cartridge, or the like, in which medicine for one dose is accommodated, is loaded to the administering device for each administration, and administration is performed (equivalent to Patent Document 1). There are so-called single-use types in the single-dose administering devices of (ii), where the entire administering device can be discarded after each single-dose use. The multi-dose administering device of (i) accommodates multiple doses worth of medicine in a single administering device, and accordingly is very useful from the perspective of portability and convenience. Meanwhile, an operation of measuring out medicine for one dose with is necessary for each administration. If this operation is not strictly carried out, there is a possibility that the necessary amount of medicine cannot be accurately measured out, and consequently the necessary amount of medicine cannot be administered each time in a stable manner. This is therapeutically unsuitable for drugs which require strict control of administration amount. Also, it is extremely difficult to maintain a sealed state for containers storing multiple doses of medicine over the entire usage period, and accordingly there is a possibility that powdered medicine of drugs which readily absorb moisture or oxidize will denature or decompose in the container during the usage period. Further, the same nozzle is repeatedly used, and the outer part of the nozzle becomes soiled with nasal discharge, medicine remains adhering on the inner part of the nozzle after administration operations, and so forth. Accordingly, the nozzle needs to be cleaned periodically. Thus, multi-dose administering devices have issues regarding the certainty of administration amount, ensuring stability of the medicine, necessity of periodic maintenance, and so forth, in that operations for measuring out the necessary amount of medicine for each dose are strict, the sealing performance of the medicine storing container is low, the nozzle needs to be periodically cleaned, and so forth.

Meanwhile, single-dose administering devices of (ii) have an advantage in that the necessary amount of medicine can be administered each time in a sure manner, since a container such as a capsule, cartridge, or the like, in which one dose of medicine is accommodated is loaded to the administering device and administration is performed, with each administration. Further, the container such as a capsule, cartridge, or the like is individually packaged and can be stored sealed until the time of use, and accordingly application to drugs that readily absorb moisture or oxidize is relatively easy. Meanwhile, a capsule is employed as the medicine container as in the device disclosed in Patent Document 1, and the operations of loading the capsule to the administering device, and removing the used capsule from the administering device after use, are necessary as prior preparation for each administration. Also, in a case where a needle is used to perforate the top and bottom of the capsule as prior preparation for each administration, there is the possibility that the medicine will be contaminated with fragments of the capsule, and the possibility that the manner of perforation will not be stable each time. Consequently, spraying characteristics of the medicine from the nozzle may not be stable. Further, the device disclosed in Patent Document 1, for example, repeatedly uses the same nozzle, and accordingly the outer part of the nozzle becomes soiled with nasal discharge, medicine remains adhering on the inner part of the nozzle after administration operations, and so forth. Accordingly, the nozzle needs to be cleaned periodically. Thus, single-dose administering devices have issues in that operations of loading and unloading a container accommodating one dose of medicine to the administering device and the task of perforating the medicine container are necessary, with each administration, periodic maintenance is necessary, and so forth.

Further, conventional devices could also include problems such as

- the manner of ejection of medicine that varies depending on actions when administering,
- the sprayer that cannot be reused in a case of a so-called single-use type, and
- the concern of the medicine being contaminated by small fragments created at the time of perforation, but there have been no improvements made in these respects, either.

Accordingly, it is an object of the present invention to provide a nozzled cartridge for storing medicine, a sprayer therefor, and a powdered medicine dispensing device for nasal cavities, having a structure capable of improved uniformity of amount administered in each dose, improved drug preservability of the preservation container, facilitating ease-of-use regarding administration operations, and improved portability, and also leading to solving other problems as well.

Solution to Problem

A nozzled cartridge for storing medicine, according to an aspect of the present invention, includes a medicine container that is to be filled with a predetermined quantity of a powdered medicine, a nozzle portion that is formed on the medicine container and that ejects the powdered medicine, a closing member that closes an opening in the nozzle portion, and a valve member that functions as a plug to close another opening in the medicine container, and that is opened when administering medicine. The nozzled cartridge is detachably mountable to a sprayer when administering medicine.

The nozzled cartridge configured thus has a medicine container that is to be filled with a predetermined quantity of a powdered medicine, and accordingly improved uniformity of amount administered in each dose and improved portability is readily realized by preferably filling with medicine for a single dose. In other words, the nozzle itself can be said to have been also imparted with a function of serving as a container for powdered medicine (including one dose worth being loaded), and it can be said that the structure facilitates realization of uniformity of amount administered in each dose, and improved portability.

Also, the nozzled cartridge configured thus also is a structure where a nozzle itself has been made into a cartridge, so reuse of the nozzle is unnecessary. This enables problems such as sanitary issues due to reusing the nozzle, such as cleaning being necessary in a case of the nozzle being soiled by nasal discharge or the like, decomposition or denaturing of residual medicine in the nozzle being administered to the body, and so forth, to be overcome.

Also, by the nozzled cartridge configured thus being preferably filled with medicine for administration of a single dose, and each cartridge being sealed until use, problems that can occur regarding drug efficacy and toxicity in relation to preservation stability within the medicine container (problems of unsuitability regarding medicines that readily exhibit decomposition or denaturing under humidity, oxygen, or the like) can be resolved. Moreover, drug preservability of the preservation container can be improved.

In the nozzled cartridge described above, an unsealable cartridge seal may be applied to an opening of the closing member.

In the nozzled cartridge described above, a retaining groove that retains the valve member may be formed at the other opening of the medicine container.

In the nozzled cartridge described above, a retaining edge portion may be formed on the valve member, for retention at a retaining portion.

In the nozzled cartridge described above, a shaft portion continuing to the retaining edge portion, and a stopper portion that is disposed on the shaft portion at a position spaced from the retaining edge portion and that has a shape that it to be hooked to a predetermined position of the other opening, may be formed on the valve member.

In the nozzled cartridge described above, an air passageway that allows passage of air may be formed on the stopper portion.

In the nozzled cartridge described above, a pointed portion that is pointed in shape from the retaining edge portion toward the opening of the nozzle portion may be formed on the valve member.

In the nozzled cartridge described above, a tapered portion may be formed between the retaining edge portion of the valve member and the shaft portion so as to have a diameter increasing from the shaft portion toward the retaining edge portion.

In the nozzled cartridge described above, a seat on which the valve member or the tapered portion thereof to abut after valve opening may be formed at the other opening of the medicine container.

In the nozzled cartridge described above, the seat may be formed to have a shape with which the valve member or the tapered portion thereof comes into planar contact.

A sprayer according to an aspect of the present invention is a sprayer that, in a state where the above-described cartridge is attached, feeds air into the cartridge and sprays the powdered medicine. The sprayer includes an air-feeding device that feeds air into the cartridge, and a pressing member that is a member performing stroke movement in conjunction with movement of the air-feeding device, and that directly or indirectly abuts the valve member at a predetermined position partway along the stroke and opens the valve member.

In the sprayer described above, a finger rest where a user can rest a finger when using the sprayer may be provided.

In the sprayer described above, a venthole may be formed in the pressing member.

In the sprayer described above, an aperture end of the venthole may be formed at an end face of the pressing member.

In the sprayer described above, the air-feeding device may include a bellows pump.

In the sprayer described above, the air-feeding device may include a cylinder and a plunger.

A powdered medicine dispensing device for nasal cavities, according to an aspect of the present invention, is configured as a combination of any one of the above-described cartridges and any one of the above-described sprayers.

A powdered medicine dispensing device for nasal cavities, according to an aspect of the present invention, is a device including, in a combination combined beforehand:

a nozzled cartridge for storing medicine, including a medicine container that is filled with a predetermined quantity of a powdered medicine, a nozzle portion that is formed on the medicine container and that ejects the powdered medicine, a closing member that closes an opening in the nozzle portion, and a valve member that functions as a plug to close another opening in the medicine container, and that is opened when administering medicine, and a sprayer that feeds air into the cartridge and sprays the powdered medicine,

Advantageous Effects of Invention

According to the present invention, there can be provided a nozzled cartridge for storing medicine, a sprayer therefor, and a powdered medicine dispensing device for nasal cavities, having a structure capable of improved uniformity of amount administered in each dose, improved drug preservability of the preservation container, facilitating ease-of-use regarding administration operations, and improved portability, and also leading to solving other problems as well.

BRIEF DESCRIPTION OF DRAWINGS

FIG. 10 is a cross-sectional view of the nozzle base, taken along line X-X in

FIG. 8.

DESCRIPTION OF EMBODIMENTS

Description of the configuration of the present invention will be made in detail below based on an example of an embodiment illustrated in the Figures.

Figure 3:
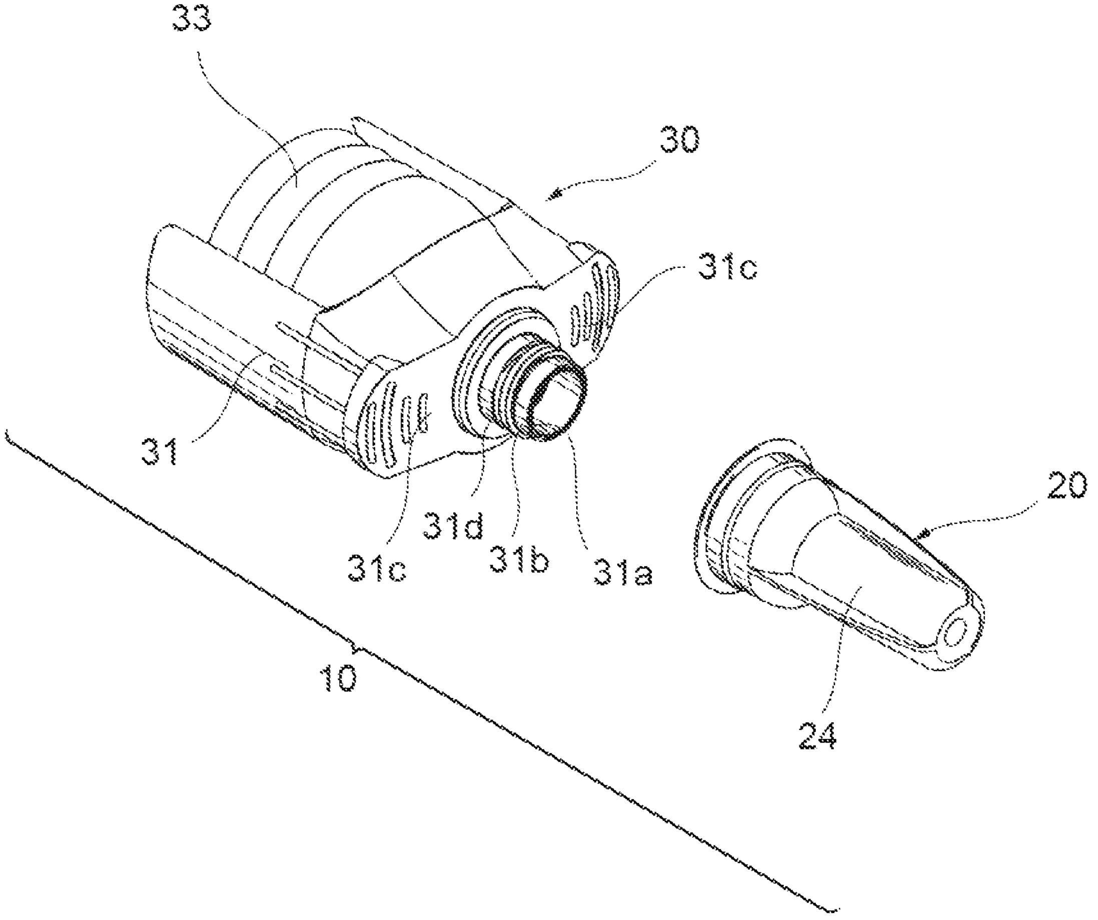
FIG. 3 is a perspective view of the nasally-administrable medicine administering device in a state with a cartridge and a sprayer separated.

A powdered medicine dispensing device for nasal cavities according to the present embodiment (hereinafter also referred to as “nasally-administrable medicine administering device”) 10 is made up of a combination of a cartridge 20 and a sprayer 30 (see FIG. 3, etc.).

<Configuration of Cartridge 20>

Figure 4:
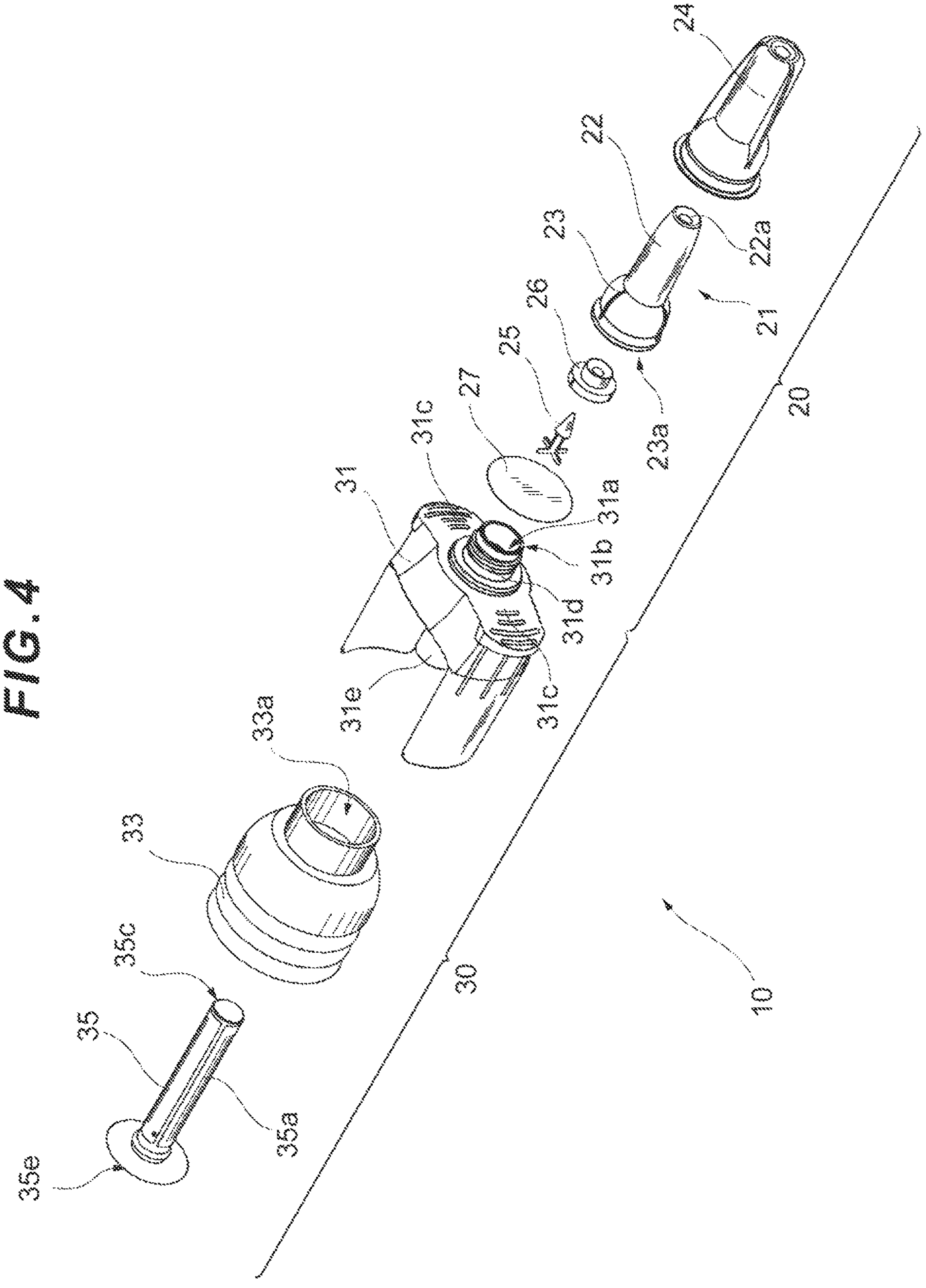
FIG. 4 is a disassembled perspective view of the nasally-administrable medicine administering device (powdered medicine dispensing device for nasal cavities).
Figure 5:
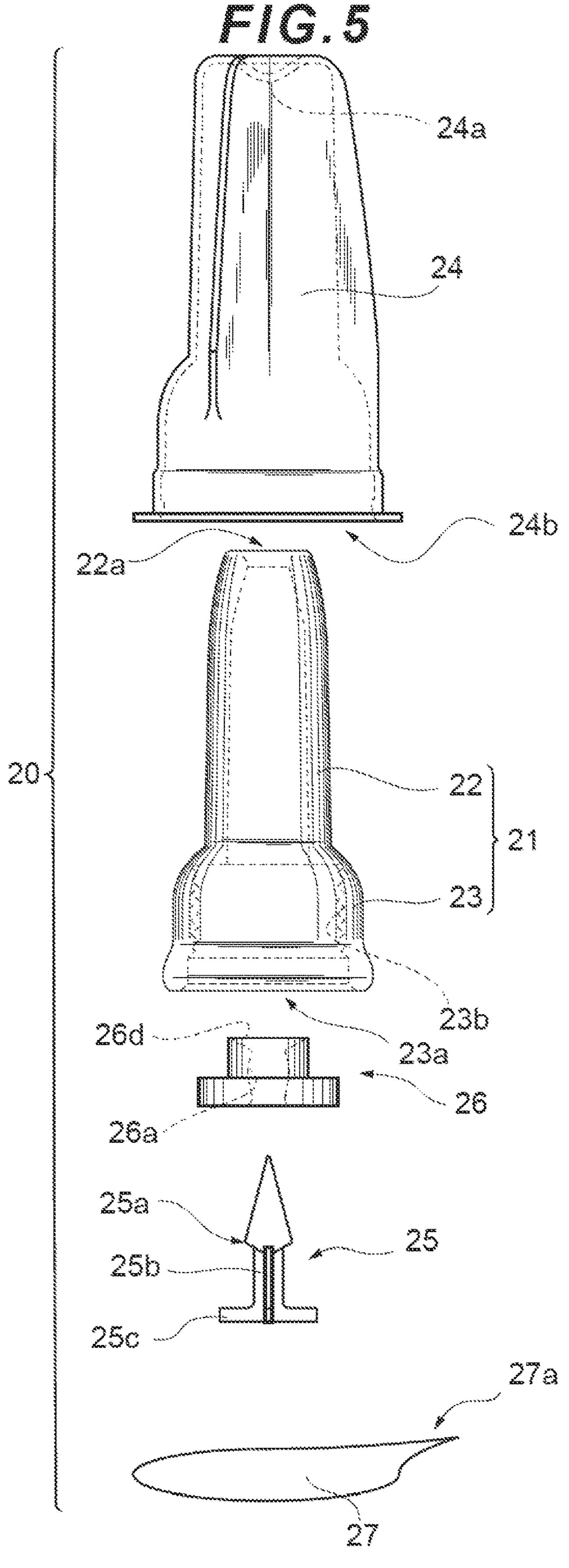
FIG. 5 is an exploded view illustrating a configuration example of a cartridge.

The cartridge 20 is a nozzled cartridge suitable for storing medicine, and is provided with a medicine container 21, a nozzle portion 22, a nozzle cover (closing member) 24, a valve member 25, a nozzle base 26, and so forth (see FIG. 4 and FIG. 5).

The medicine container 21 is a container that is filled inside with a predetermined quantity of a powdered medicine M. The medicine container 21 according to the present embodiment is provided with the nozzle portion 22 formed in a tapered shape for example, and a cylindrical base portion 23 continuing to the nozzle portion 22, and functions as a nozzle-cum-medicine-container that also has functions of a nozzle (see FIG. 5, etc.).

The nozzle portion 22 of the medicine container 21 has a tapered shape to facilitate dispensing powdered pharmaceuticals into the nasal cavities of the patient, and has an appropriate roundness formed near the tip as necessary. An opening 22*a*, from which the powdered medicine M is ejected, is provided at the center of the tip of the nozzle portion 22 (see FIG. 5, etc.).

A stepped inner space where the nozzle base 26 is mounted is formed on the inner side of the cylindrical base portion 23 of the medicine container 21 (see FIG. 5). Also, a screw portion (which alternatively may be a stepped portion) 23*b* used to screw the medicine container 21 and nozzle cover 24 together so as to be integrated in a detachably mounted state is formed on the inner peripheral face (inner wall) of the cylindrical base portion 23 (see FIG. 5).

The nozzle cover 24 is a cover member that covers the medicine container 21 (see FIG. 4, etc.). The nozzle cover 24 according to the present embodiment is provided on the inner side thereof with a closing protrusion 24*a* that closes the opening 22*a* of the nozzle portion 22 (see FIG. 5), configured to function as a member that closes the medicine container 21 (medicine container plug). A cartridge seal 27 is applied to an opening 24*b* of the nozzle cover 24.

The cartridge seal 27 is a member that seals the inner space of the nozzle cover 24, and is applied to the opening 24*b* of the nozzle cover 24. A tab 27*a* may be formed on the edge portion of the cartridge seal 27, to facilitate peeling away by a user such as a patient at the time of use (see FIG. 5, etc.).

The valve member 25 is a member that functions as a plug that closes another opening 23*a* of the medicine container 21, and opens when administering medicine. The valve member 25 according to the present embodiment has a structure provided with a retaining edge portion 25*a*, a shaft portion 25*b*, stopper portions 25*c*, air passageways 25*d*, a pointed portion 25*e*, and air passage grooves 25*f* (See FIG. 6 and FIG. 7, etc.).

Figure 6:
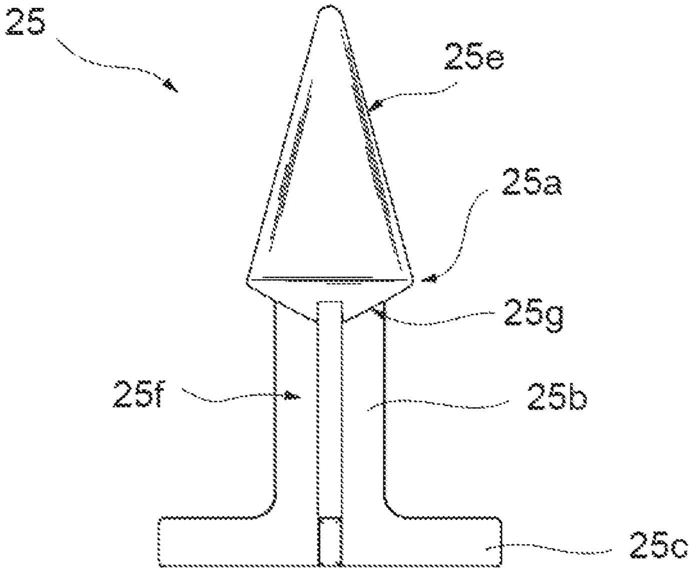
FIG. 6 is a front view illustrating a configuration example of a valve member.
Figure 7:
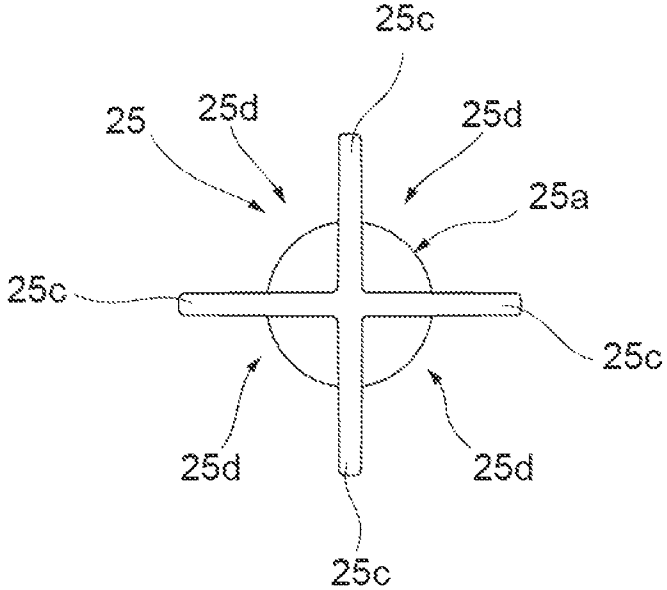
FIG. 7 is a bottom view of the valve member.
Figure 8:
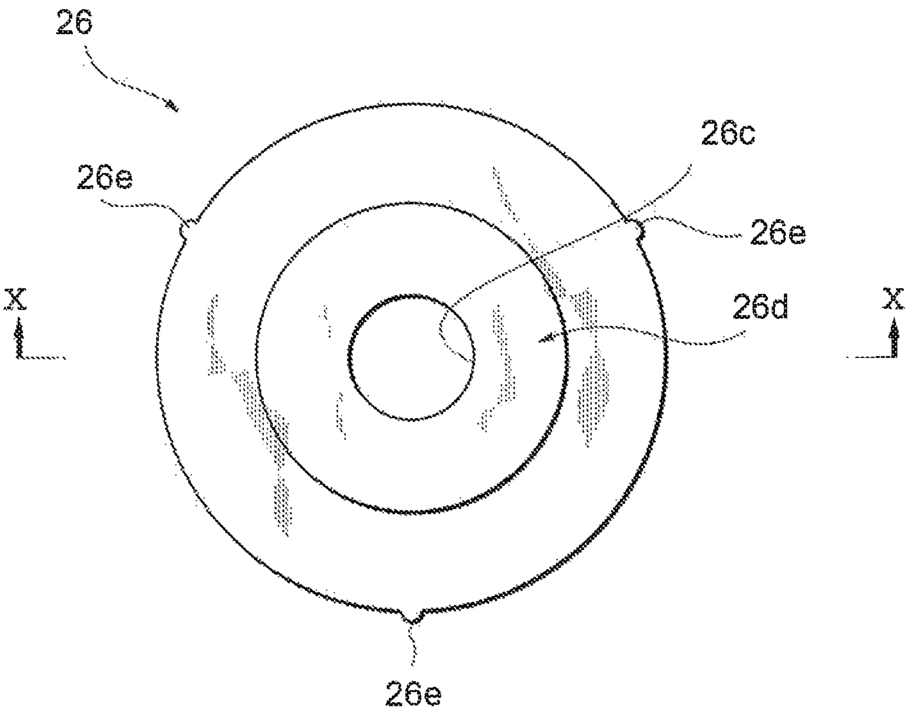
FIG. 8 is a plan view illustrating a configuration example of a nozzle base.
Figure 9:
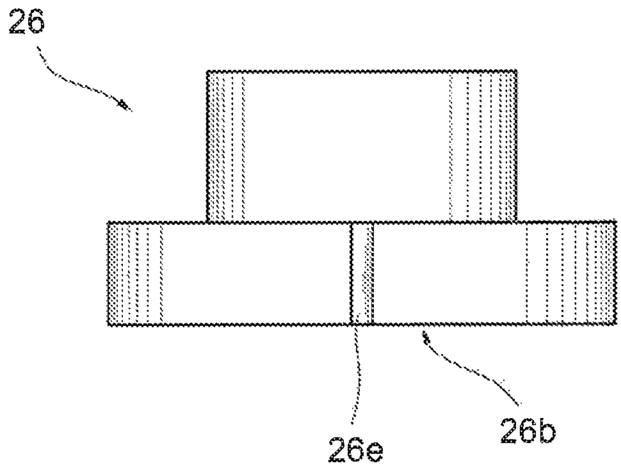
FIG. 9 is a front view of the nozzle base.

The retaining edge portion 25*a* is made up of a large-diameter portion that protrudes to the outer periphery side so as to be retained at the other opening 23*a* of the medicine container 21 (see FIG. 6, etc.). The present embodiment has a configuration where a retaining groove 26*a* is formed in the nozzle base 26 that is mounted to the opening 23*a*, so that the retaining edge portion 25*a* of the valve member 25 is retained at this retaining groove 26*a* in an airtight or sealed state (see FIGS. 16A, 16B, etc.). The other opening 23*a* of the medicine container 21 is in an airtight or sealed state in a state where the retaining edge portion 25*a* is retained at the retaining groove 26*a*.

Figure 14:
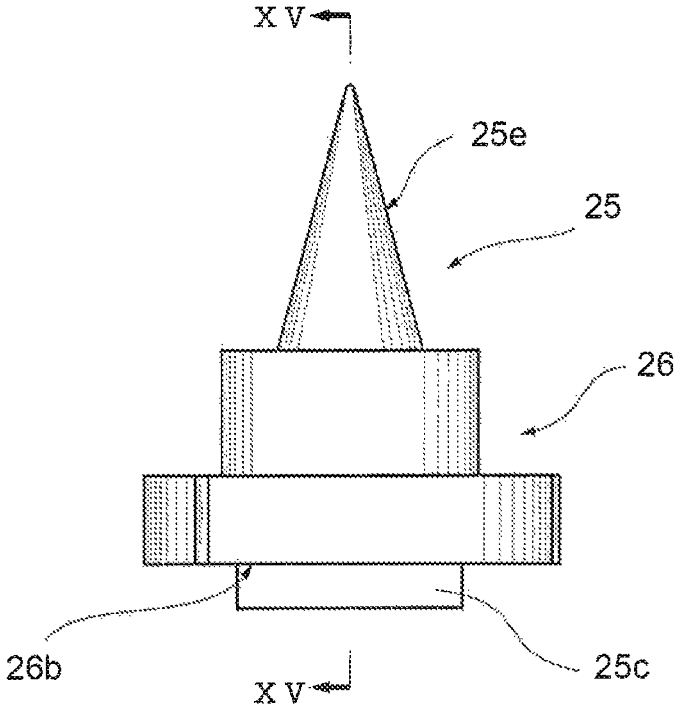
FIG. 14 is a front view illustrating the valve member and the nozzle base in an open-valve state.

The shaft portion 25*b* of the valve member 25 is configured of a shaft continuing to the retaining edge portion 25*a*, The stopper portions 25*c* are formed at an end portion of the shaft portion 25*b* (position distanced from the retaining edge portion 25*a*). The stopper portions 25*c* are formed to have a shape and size to abut on and to be hooked to a predetermined position of the other opening 23*a*, such as an abutting portion 26*b* of the nozzle base 26 that is mounted to the other opening 23*a* for example (see FIG. 14, etc.). The stopper portions 25*c* and shaft portion 25*b* according to the present embodiment are formed having a cross-like shape, with the air passageways 25*d* each formed at the stopper portions 25*c* and the air passage grooves 25*f* each formed around the shaft portion 25*b* following the axial direction (see FIG. 6 and FIG. 7, etc.). In a state where the valve member 25 is open, air can flow from the outside to inside of the nozzle portion 22, passing through the aforementioned air passageways 25*d* and air passage grooves 25*f* (see FIGS. 17A, 17B).

Also, the pointed portion 25*e* and a tapered portion 25*g* are formed to the valve member 25. The pointed portion 25*e* is formed having a shape that narrows to a point from the retaining edge portion 25*a* toward the opening 22*a* of the nozzle portion 22 (tapered shape), suppressing inward vortex airflow from being formed in the air passing through when the valve is open, and consequently suppressing the powdered medicine M from being retained within the nozzle due to the vortex airflow (see FIG. 6 and FIGS. 17A, 17B, etc.). The tapered portion 25*g* is formed between the retaining edge portion 25*a* and the shaft portion 25*b*, enlarging in diameter from the shaft portion 25*b* toward the retaining edge portion 25*a*, and disperses air passing through when the valve is open to obtain a more uniform flow.

The nozzle base 26 is a member mounted to the other opening 23*a* of the medicine container 21. The present embodiment is configured such that the valve member 25 is retained at the nozzle base 26 for a valve-closed state, and restricts the operating range of the valve member 25 when the valve is open. The nozzle base 26 according to the present embodiment has a stepped shape, and is provided with the retaining groove 26*a*, the abutting portion 26*b*, a through hole 26*c*, a seat 26*d*, and ribs 26*e* (see FIG. 8 through FIG. 15, etc.).

Figure 10:
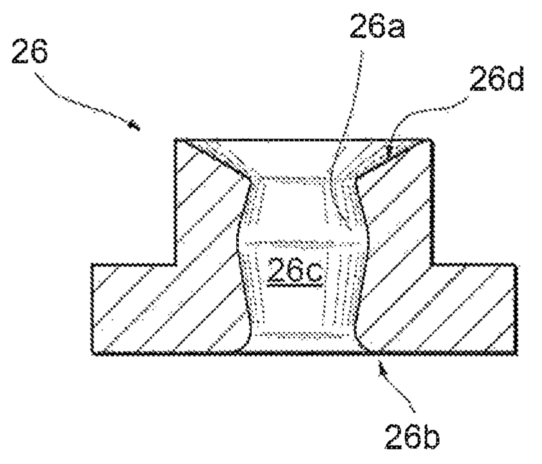
Figure 11:
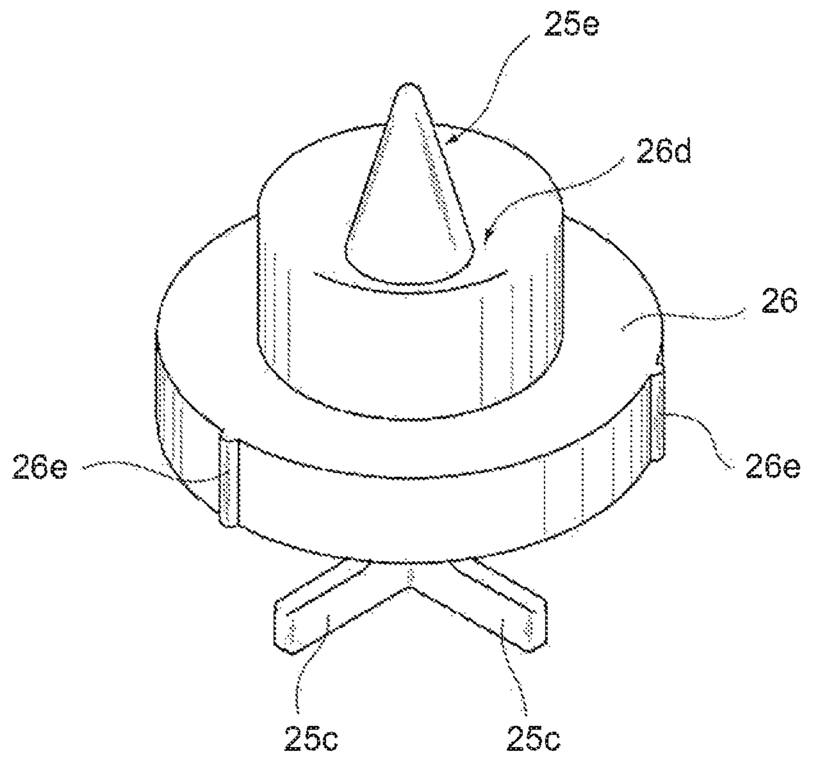
FIG. 11 is a perspective view illustrating the valve member and the nozzle base in a closed-valve state.
Figure 12:
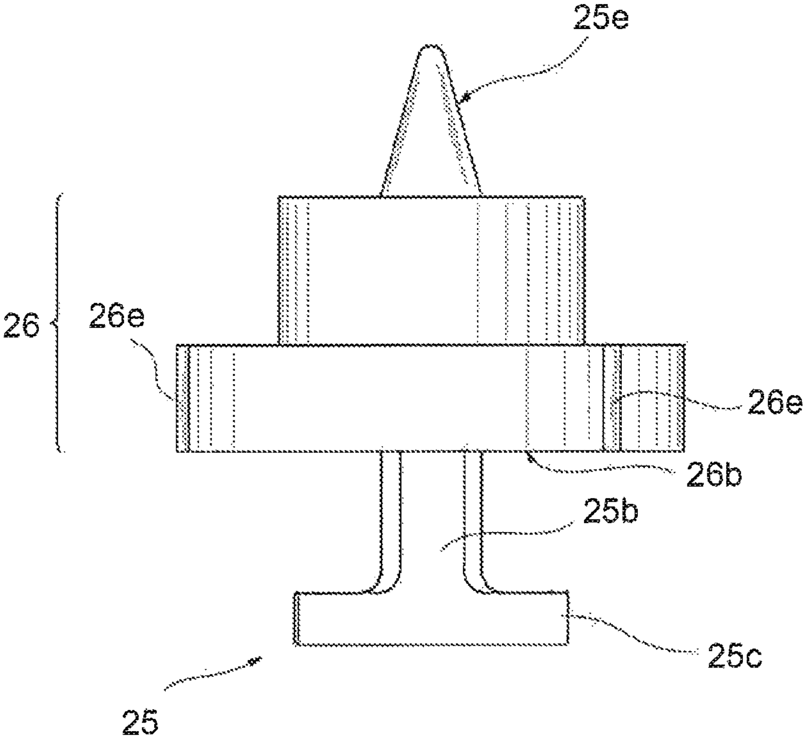
FIG. 12 is a front view illustrating the valve member and the nozzle base in a closed-valve state.
Figure 13:
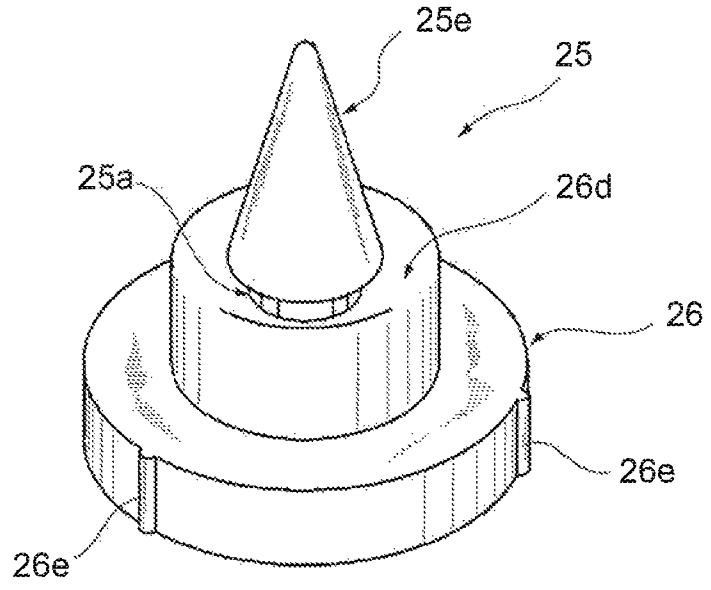
FIG. 13 is a perspective view illustrating the valve member and the nozzle base in an open-valve state.
Figure 15:
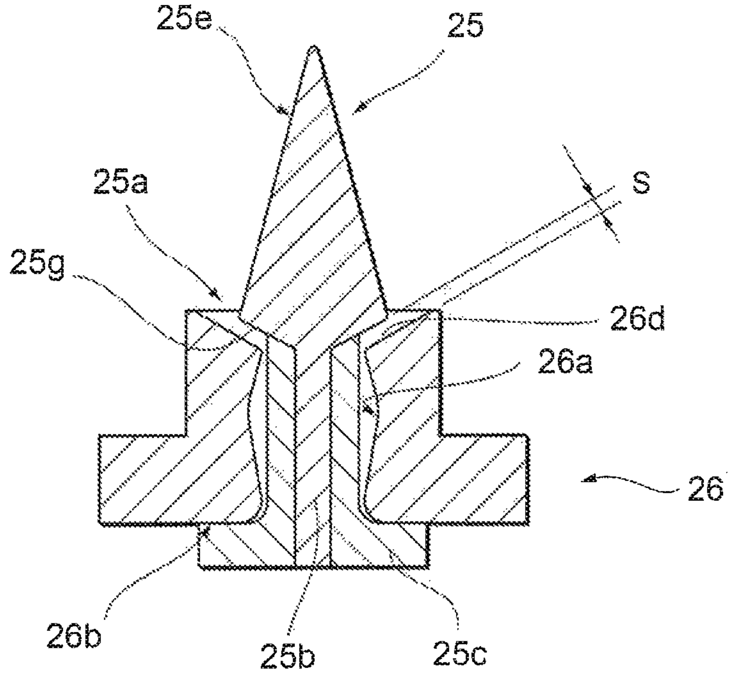
FIG. 15 is a cross-sectional view of the valve member and the nozzle base in an open-valve state, taken along line XV-XV in FIG. 14.

The retaining groove 26*a* is formed by partially enlarging the inner diameter partway along the through hole 26*c* formed in the center of the nozzle base 26 (see FIG. 10 and FIG. 15, etc.). The retaining groove 26*a* is formed such that the retaining edge portion 25*a* of the valve member 25 is retained in an airtight state (valve-closed state), and the retaining edge portion 25*a* exits the retaining groove 26*a* and the valve member 25 moves in the axial direction when the valve is open. Part or all of the nozzle base 26 including the retaining groove 26*a* and so forth may be formed of a material having flexibility or elasticity, so as to be capable of a certain degree of deformation when pressure is applied.

The abutting portion 26*b* restricts the operating range of the valve member 25 when the valve member 25 moves in the axial direction. In the present embodiment, a portion of the bottom face of the nozzle base 26 that is the portion where the stopper portions 25*c* of the valve member 25 abut functions as the abutting portion 26*b* (see FIG. 15, etc.). An annular gap S through which air can pass is formed between the seat 26*d* of the nozzle base 26 and the tapered portion 25*g* of the valve member 25 in a state where the stopper portions 25*c* of the valve member 25 have abutted the abutting portion 26*b* (see FIG. 15, etc.).

Figure 18B:
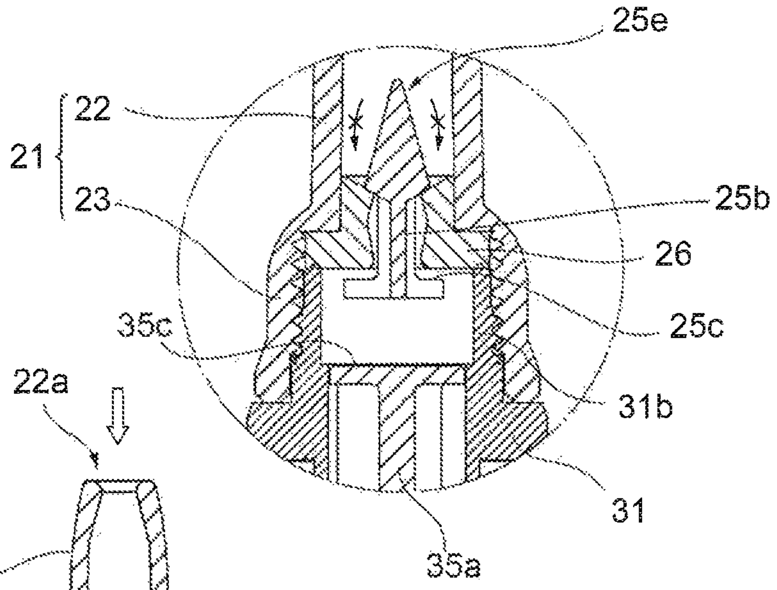
FIG. 18B is a partially enlarged view of the valve member and so forth.
Figure 18A:
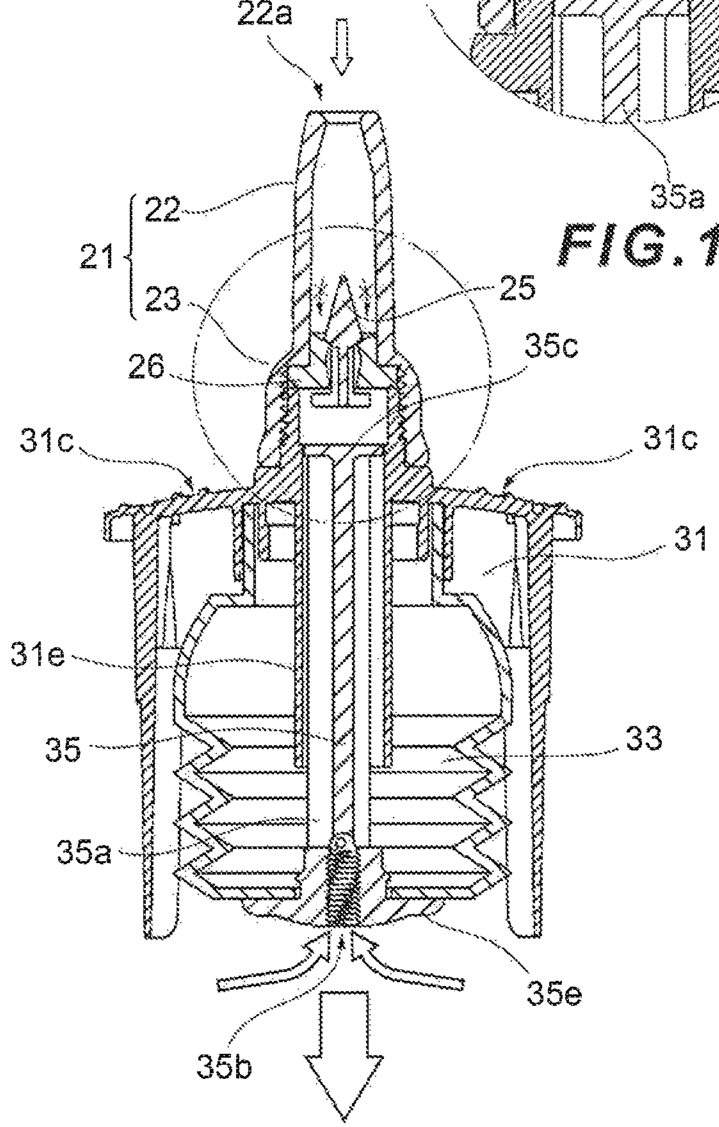
FIG. 18A is a longitudinal-section view illustrating the internal structure of the nasally-administrable medicine administering device at the time of the pump that had been compressed returning.

The seat 26*d* is formed as a region that part of the valve member 25 abuts when the valve member 25 returns back toward the sprayer 30 after opening of the valve. Abutting part of the valve member 25 against the seat 26*d* enables leakage of remaining medicine from the medicine container 21 to be suppressed during reverse flow of air following spraying of the medicine (See FIGS. 18A, 18B, etc.). This seat may be directly formed on (the other opening 23*a* of) the medicine container 21, but in the present embodiment, a countersunk inclined face is provided to one opening of the nozzle base 26, thereby forming the seat 26*d* with which the tapered portion 25*g* of the valve member 25 comes into planar contact (FIG. 15 and FIGS. 18A, 18B, etc.). Implementing planar contact facilitates suppression of leakage of remaining medicine.

The ribs 26*e* are made up of protrusions provided to fix the nozzle base 26 within the medicine container 21. The ribs 26*e* are equidistantly disposed at three positions on the outer periphery of the nozzle base 26 in the present embodiment, as one example (see FIG. 8 and FIG. 9).

<Configuration of Sprayer 30>

The sprayer 30 is used when feeding air into the cartridge 20 and spraying the powdered medicine M in a state where the cartridge 20 such as described above is attached, and is provided with, for example, a body 31, a bellows pump (air-feeding device) 33, a rod (pressing member) 35, and so forth (see FIG. 4).

The air-feeding device is a device for feeding air into the cartridge 20. The bellows pump 33 that feeds out air when being compressed, and suctions in air when being restored to the original form from the compressed state by elastic force, is employed in the present embodiment as an example of the air-feeding device (see FIG. 4 and FIGS. 16A, 16B, etc.).

The rod 35 is a member that is disposed within the bellows pump 33 in a state where a tip portion 35*c* thereof protrudes from an opening 33*a* of the bellows pump 33, and that is plunged at the time of administering medicine, and also performs stroke movement in conjunction with the restoring action of the bellows pump 33. The rod 35 is formed to a length so as to abut (the stopper portions 25*c* of) the valve member 25 at a predetermined position partway through the stroke action, and plunge the valve member 25 to physically open the valve (see FIGS. 16A, 16B and FIGS. 17A, 17B, etc.).

Formed on the rod 35 are, in addition to the tip portion 35*c*, a shaft portion 35*a*, a thumb rest 35*e*, an aperture 35*d*, and an aperture end 35*b*. The shaft portion 35*a* connects between the tip portion 35*c* and thumb rest 35*e*, and is formed to have a size and shape where air can pass around (more specifically, through a gap between itself and a sleeve portion 31*e* of the body 31), such as a cross-like cross-section, for example.

The thumb rest 35*e* of the rod 35 is formed to have a shape that facilitates users such as a patients or the like (physicians and the like dispensing medicine to patients are also included in users) themselves placing their thumb thereupon and plunging of the rod 35 and bellows pump 33 (e.g., a shape where a flange is formed and the contact region with the thumb is broadened, a shape where the face of contact with the thumb is gently bulged, etc.) (see FIG. 4 and FIGS. 16A, 16B, etc.).

The aperture 35*d* of the rod 35 is formed in the center, for example, of the thumb rest 35*e*, so that the aperture end 35*b* is naturally closed off by the thumb when the user presses the rod 35 and bellows pump 33. Note that after the user has pressed the rod 35 and bellows pump 33 to the end, the thumb is relaxed, and air can flow in from the aperture end 35*b* in this state (see FIGS. 18A, 18B). Note that air that has flowed in from the aperture end 35*b* passes through the aperture 35, 35 *d*, and thereafter passes around the shaft portion 35*a*.

The body 31 is an enclosure to which the bellows pump 33 and rod 35 are attached. Formed on the body 31 are a body opening 31*a*, a cylindrical portion 31*b*, finger rests 31*c*, a screw portion 31*d*, and the sleeve portion 31*e* (see FIG. 4, etc.).

The body opening 31*a* communicates with the opening 33*a* of the bellows pump 33, and passes air in and out as the bellows pump 33 is expanded and compressed. The screw portion 31*d* is formed on the cylindrical portion 31*b* where the body opening 31*a* is formed, enabling the cartridge 20 to be attached using a threaded structure including the screw portion 23*b* formed on the inner peripheral face of the cylindrical base portion 23, for example.

Figure 19:
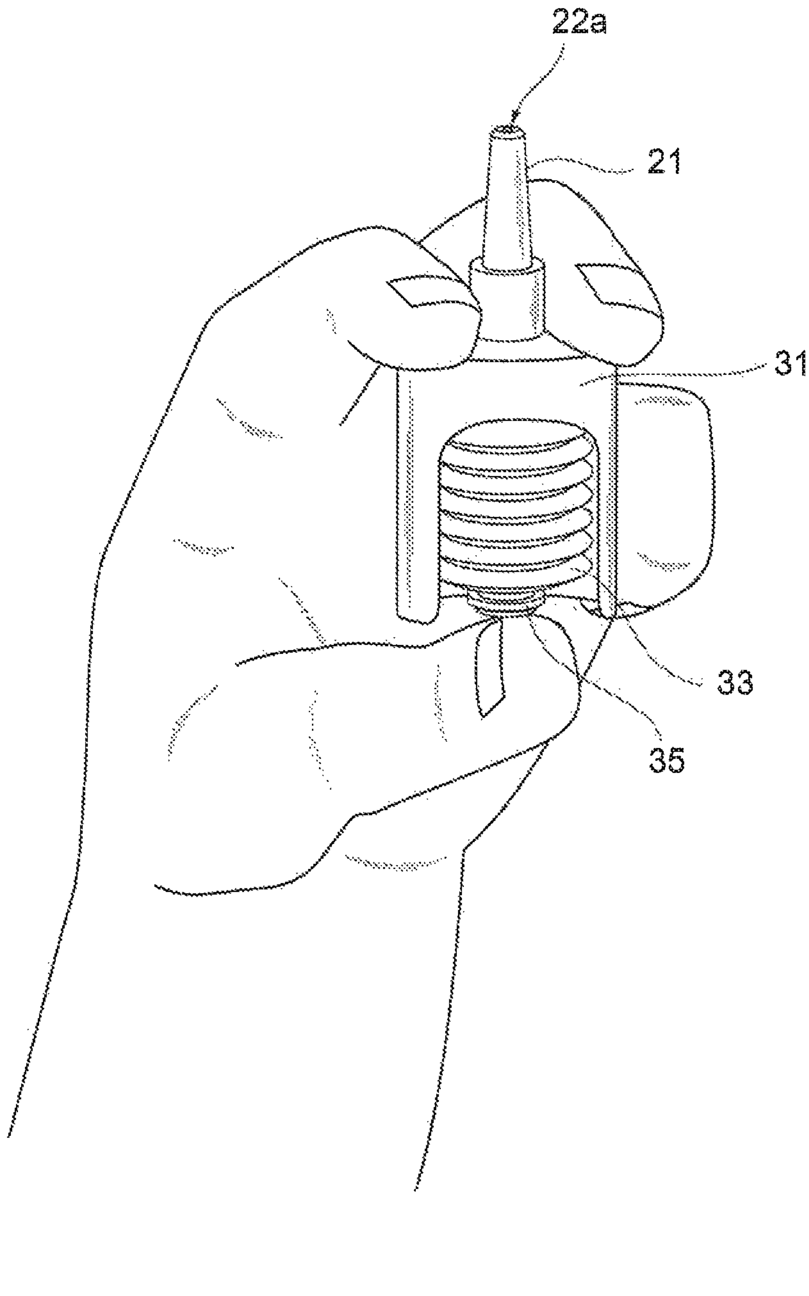
FIG. 19 is a diagram illustrating a state where the nasally-administrable medicine administering device is held pinched between fingers and thumb of a user.
Figures 20A, 20B, 20C:
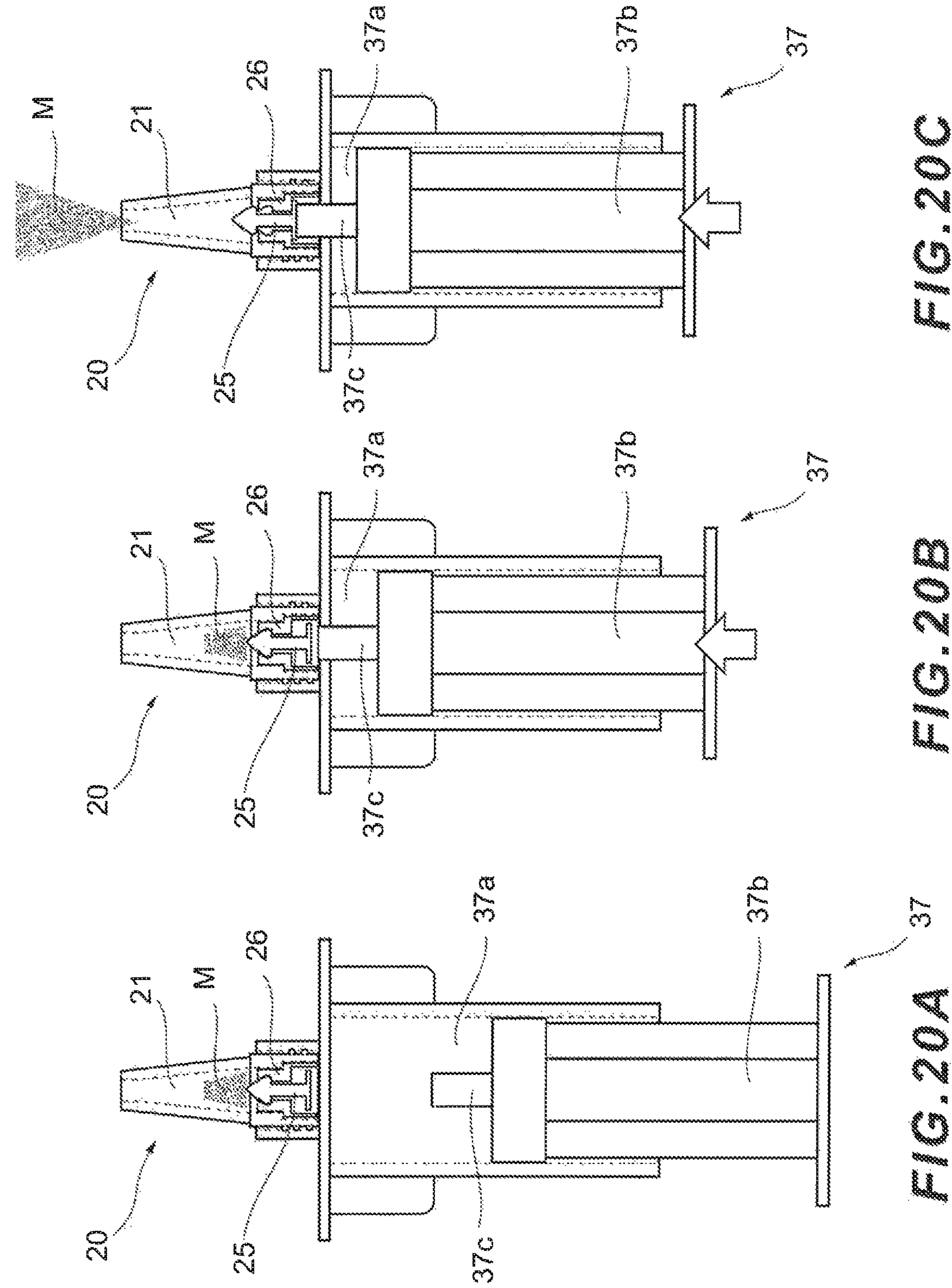
FIGS. 20A through 20C are drawings illustrating, with regard to an example of the nasally-administrable medicine administering device using a cylinder-type pump as an air-feeding device, the states of (A) before plunging a cylinder (FIG. 20A), (B) partway through plunging the cylinder (FIG. 20B), and (C) when having opened the valve member by plunging the cylinder (FIG. 20C).

Two fingers other than the thumb (normally the index finger and middle finger) are placed on the finger rests 31*c*, thereby gripping the nasally-administrable medicine administering device 10 between these fingers and the thumb placed against the thumb rest 35*e*, and plunging the rod 35 in this state enables the powdered medicine M to be ejected (see FIG. 19).

Figure 16B:
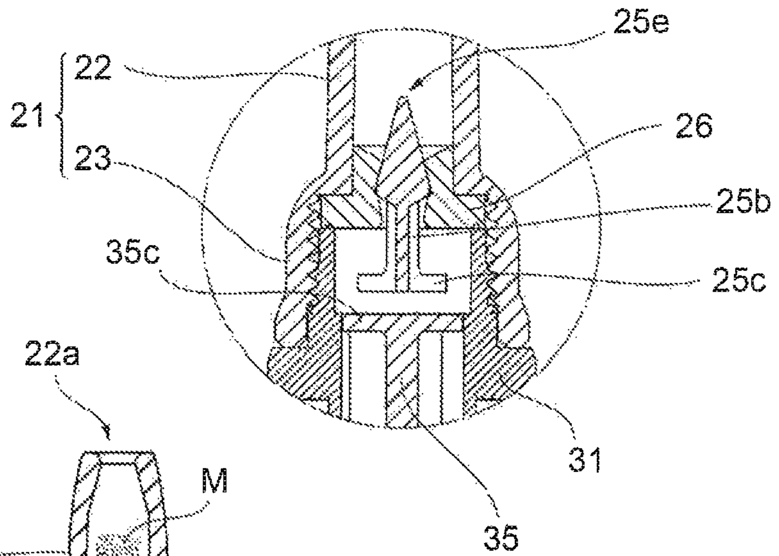
FIG. 16B is a partially enlarged view of the valve member and so forth.
Figure 16A:
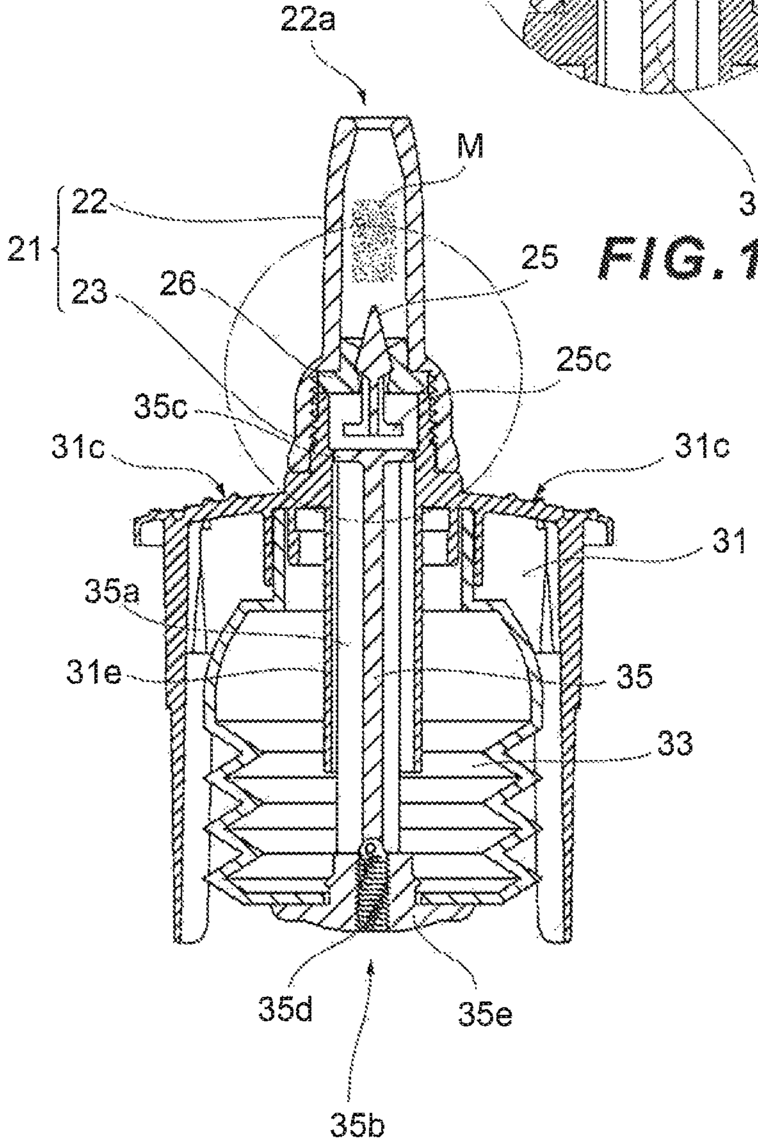
FIG. 16A is a longitudinal-section view illustrating the internal structure of the nasally-administrable medicine administering device before pump compression.

The sleeve portion 31*e* is a cylindrical portion that continues from the cylindrical portion 31*b* and extends in the opposite direction from the body opening 31*a* (see FIG. 4 and FIGS. 16A, 16B, etc.). The sleeve portion 31*e* is formed so that the inner diameter is slightly larger than the outer diameter of the rod 35, and functions as a guide so the rod 35 disposed on the inner side thereof moves straight without deviating laterally when performing stroke movement in the axial direction (see FIGS. 16A, 16B and FIGS. 17A, 17B, etc.).

<Using the Nasally-Administered Medicine Administering Device 10>

How to use the nasally-administrable medicine administering device 10, actions, and so forth, will be described (see FIG. 16A through FIG. 18B, etc.).

Figure 1:
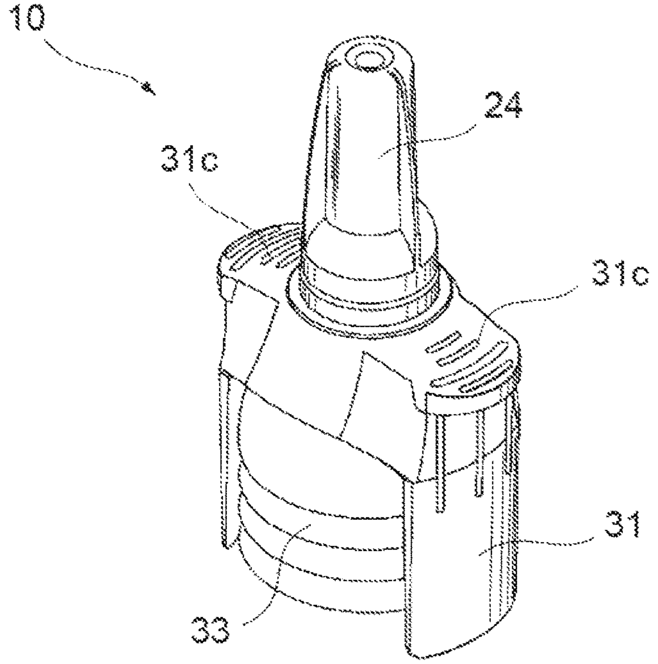
FIG. 1 is a perspective view illustrating a nasally-administrable medicine administering device (powdered medicine dispensing device for nasal cavities) according to an embodiment of the present invention.
Figure 2:
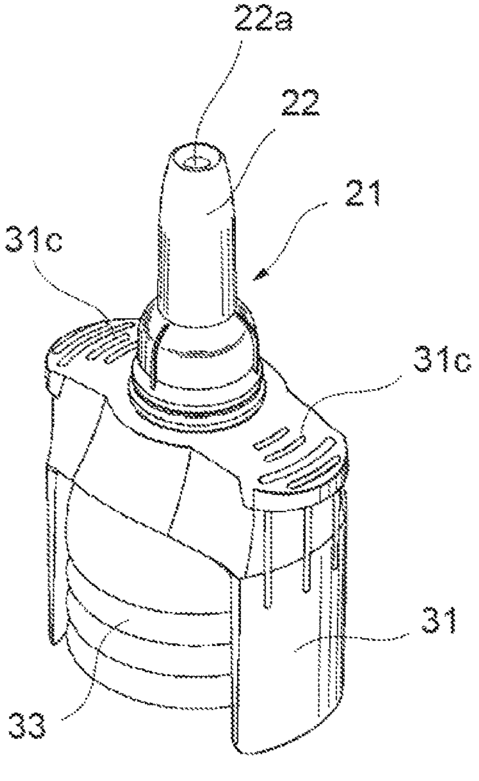
FIG. 2 is a perspective view of the nasally-administrable medicine administering device in a state with a nozzle cover removed.

The cartridge seal 27 is peeled away from the nozzle cover 24, the cartridge 20 is attached to the sprayer 30 (see FIG. 1 and FIG. 3), and the nozzle cover 24 is removed (see FIG. 2). The cartridge 20 functions as a sealed container until the cartridge seal 27 and nozzle cover 24 are removed, and has excellent preservability of the powdered medicine M. The cartridge 20 also functions as a sealed container for a short time even without the cartridge seal 27, not to mention as an airtight container, so powdered medicine M readily affected by oxygen and humidity can be easily handled.

In the state before compressing the bellows pump 33, the valve member 25 is fixed at the nozzle base 26, and in an unopened state (valve-closed state) (see FIGS. 16A, 16B). In this state, the user grips the nasally-administrable medicine administering device 10 with the fingers and thumb (see FIG. 19), and directs the nozzle portion 22 toward the nostrils.

When the user presses the rod 35 upwards by the thumb, the bellows pump 33 and air therein is compressed in a state where the aperture end 35*b* is closed off by the thumb. Further pressing the rod 35 up to a predetermined position abuts the tip portion 35*c* thereof against (the stopper portions 25*c* of) the valve member 25, physically plunging the valve member 25.

Figure 17B:
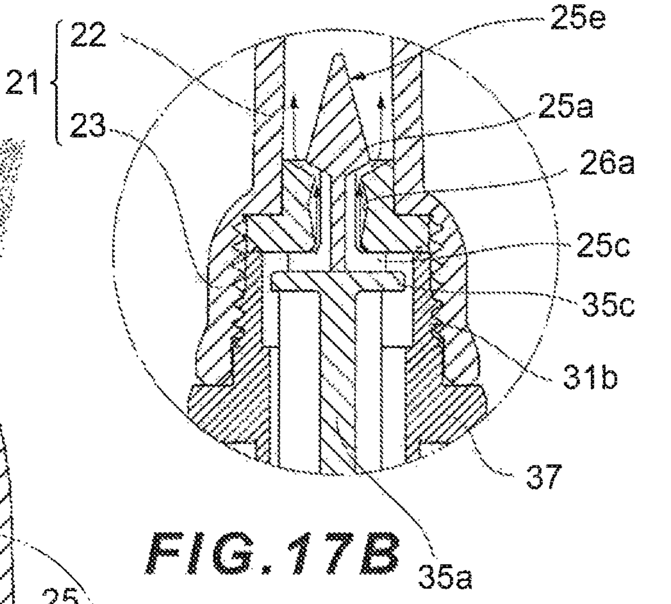
FIG. 17B is a partially enlarged view of the valve member and so forth.
Figure 17A:
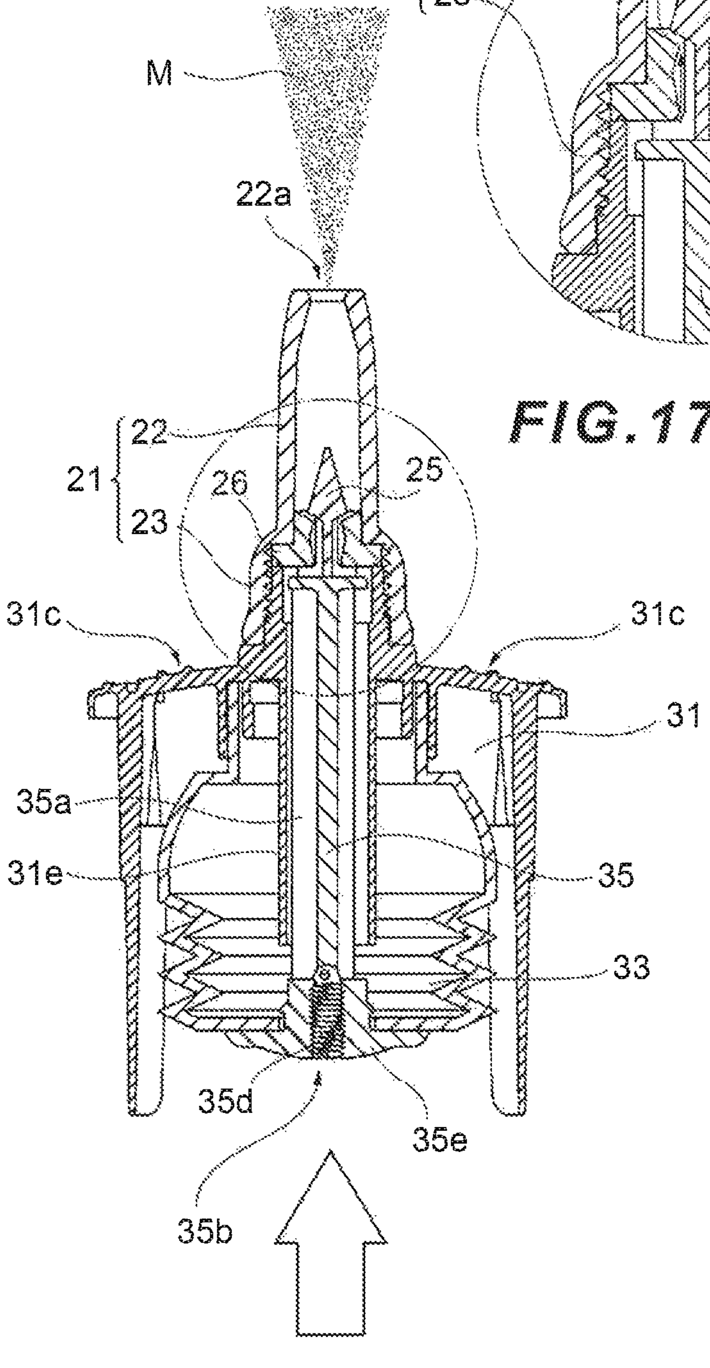
FIG. 17A is a longitudinal-section view illustrating the internal structure of the nasally-administrable medicine administering device during pump compression.

When physically plunged by the rod 35, the retaining edge portion 25*a* of the valve member 25 exits the retaining groove 26*a* of the nozzle base 26, and the valve member 25 is in an open state (valve-opened state) (see FIG. 15 and FIGS. 17A, 17B). Immediately after the valve member 25 is opened, the movement of the valve member 25 and the rod 35 plunging the valve member 25 is restricted when the stopper portions 25*c* abut the abutting portion 26*b*.

When the valve member 25 is in an open state (valve-opened state), air within the bellows pump 33 flows into the medicine container 21 through the air passageways 25*d*→the air passage grooves 25*f*→the gap S (between the seat 26*d* of the nozzle base 26 and the tapered portion 25*g* of the valve member 25), causing the powdered medicine M to be ejected from the opening 22*a* of the nozzle portion 22 (see FIG. 15 and FIGS. 17A, 17B). At this time, the pointed portion 25*e* of the valve member 25 restricts inward vortex airflow from being formed in the air passing through when the valve is open, consequently suppressing the powdered medicine M from being retained within the nozzle due to the vortex airflow. Accordingly, the powdered medicine M is efficiently ejected to the outside of the nozzle.

Also, the tapered portion 25*g* forms airflow following the inner wall of the nozzle, so spraying that is more uniform and highly efficient can be realized.

After ejecting of the powdered medicine M, when the user relaxes the thumb, the bellows pump 33 is restored to the original form by elastic force thereof, and the rod 35 performs stroke movement to the original position in conjunction with this movement. At this time, the valve member 25 is pulled in by airflow that is opposite to that of when ejecting medicine and returns, and the tapered portion 25*g* thereof comes into planar contact with the seat 26*d* and is in a close contact state, and thus functions as a check valve. Accordingly, residual medicine remaining in the medicine container 21 without having been ejected is suppressed from being drawn into the bellows pump 33 (see FIGS. 18A, 18B).

<Features of Nasally-Administered Medicine Administering Device 10>

Features of the nasally-administrable medicine administering device 10 according to the present embodiment that has been described so far will be set forth below.

While conventional devices that reuse the nozzle have had sanitary issues (cleaning is necessary in a case of the nozzle being soiled by nasal discharge or the like), the nasally-administrable medicine administering device 10 according to the present embodiment employs the nozzled cartridge 20 (making the nozzle itself to be part of the cartridge) for a single-use arrangement, and accordingly, issues occurring in cases of reusing cannot occur.

Also, while conventional devices that reuse the nozzle have had issues in that medicine remaining inside the nozzle decomposes or denatures, and the decomposed material or denatured material is administered (cleaning of the nozzle is necessary), the nasally-administrable medicine administering device 10 according to the present embodiment makes the nozzle itself to be part of the cartridge for a single-use arrangement, and accordingly, such issues occurring in cases of reusing cannot occur.

While conventional devices have had issues regarding securing preservation stability regarding drugs with low preservation stability in the medicine container (unsuitable for medicine that readily exhibits decomposition or denaturing under humidity, oxygen, etc.), in the nasally-administrable medicine administering device 10 according to the present embodiment the nozzle cover 24 is sealed by the cartridge seal 27 so as to function as a sealed container, so that such issues do not occur. The cartridge 20 also functions as a sealed container for a short time even without the cartridge seal 27, not to mention as an airtight container. Accordingly, medicine that is susceptible to oxygen and humidity is also readily applicable.

While conventional devices have had issues in that medicine falls into the pump or inside of the device, resulting in less amount being sprayed, or medicine that has fallen being additionally administered at the time of the subsequent administration, and the administration amount is not stable, in the nasally-administrable medicine administering device 10 according to the present embodiment spraying is started at the same time as the valve member 25 being opened, and the valve member 25 functions as a check valve when the bellows pump 33 is being restored, so the chance of medicine being drawn into the bellows pump 33 is extremely small.

While conventional devices have had issues in that fragments of the container are created at the time of puncturing the seal or piercing the capsule with a needle or the like to open an air channel hole in the closure of the medicine container, and are administered to the body, the nasally-administrable medicine administering device 10 according to the present embodiment does not puncture a seal or pierce a capsule with a needle or the like, so such issues cannot occur.

While conventional devices have had drug efficacy related issues in that the way air holes are opened at the time of opening air channel holes in the closure of the medicine container is not uniform, and consequently the manner of spraying the medicine varies, the nasally-administrable medicine administering device 10 according to the present embodiment is of a configuration where only the sprayer 30 is reusable, so a similar airflow channel is formed each time (each medicine administration), and medicine can be administered with a stable manner of spraying.

While conventional devices have had issues in that the manner of spraying varies depending on how the pump is pressed, in the nasally-administrable medicine administering device 10 according to the present embodiment the valve member 25 is opened under a constant air pressure, the stroke amount of the rod 35 and amount of extending and compressing of the bellows pump 33 are fixed quantities, and the flow is under a constant air pressure and air quantity, so the manner of spraying is stable.

While there have been cases where preparation before administration, including operations of attaching the capsule or cartridge, is cumbersome in conventional devices, operations of attaching the cartridge 20 to the sprayer 30 in the nasally-administrable medicine administering device 10 according to the present embodiment are completed by peeling the cartridge seal 27 away from the cartridge 20, attaching to the sprayer 30, and removing the nozzle cover 24, and accordingly is easy to use. That is to say, conventional devices require a process for administration of (1) removing the capsule from PTP packaging→(2) removing the nozzle→(3) loading the capsule to inside of the administering device (inside the nozzle)→(4) attaching the nozzle (5) attaching the nozzle cap so as to penetrate the capsule with the needle attached within the nozzle cap, and perforate→(6) remove the nozzle cap→(7) pressing the pump to administer, as in Patent Document 1 for example. In comparison, the nasally-administrable medicine administering device 10 according to the present application only involves the operations of (1) peeling away the cartridge seal 27→(2) attaching the cartridge 20 to the sprayer 30→(3) removing the nozzle cover 24→(4) pressing the bellows pump 33 to administer.

Note that while the above-described embodiment is an example of a preferred implementation of the present invention, this is not restrictive, and various types of modifications can be made without departing from the scope of the present invention. For example, although no description was made in particular in the above-described embodiment regarding the material of the members making of the cartridge 20 and sprayer 30, commonly-used resin materials or the like may be used.

Figure 21A:
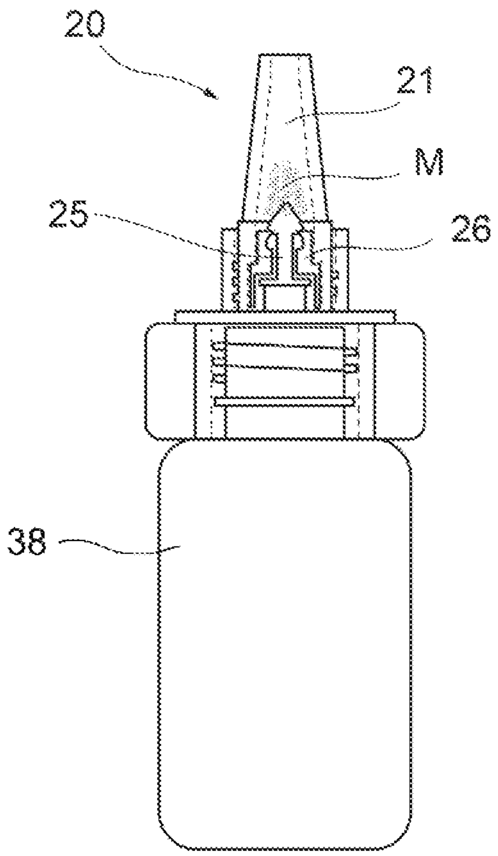
FIGS. 21A and 21B are drawings illustrating, with regard to an example of the nasally-administrable medicine administering device using a pump as an air-feeding device, the states of (A) before crushing the pump (FIG. 21A), and (B) when having crushed the pump (FIG. 21B).
Figure 21B:
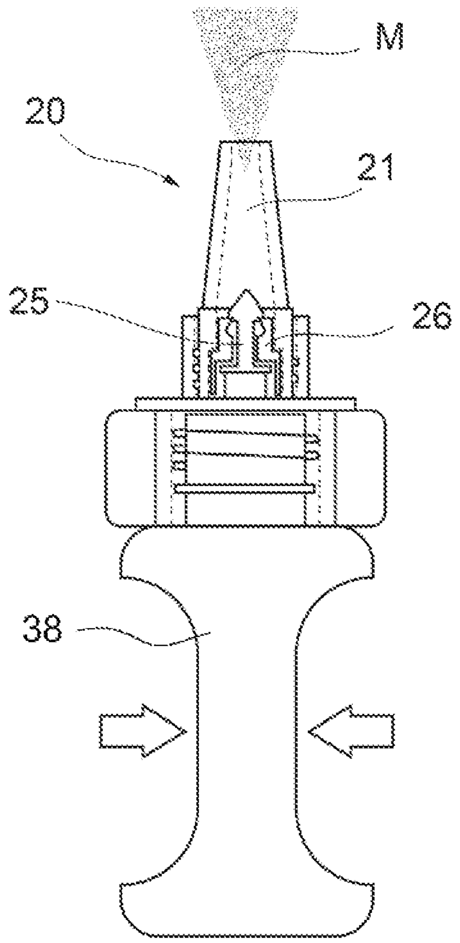

Also, although description has been made in the above-described embodiment regarding an arrangement where the bellows pump 33 is used as an example of the air-feeding device making up the sprayer 30, this is but one suitable example. Alternatively, a cylinder type pump 37 including a cylinder 37*a* and plunger 37*b* may be used as the air-feeding device, for example (see FIGS. 20A through 20D). A plunging protrusion 37*c* that physically plunges the valve member 25 may be formed on the tip of the plunger 37*b*. Such a cylinder type pump 37 can be used multiple times by replacing the cartridge 20. Note however, that the position of the plunger 37b needs to be returned before use. Alternatively, a pump 38 that is gripped and crushed to feed air may be used as the air-feeding device (see FIGS. 21A and 21B).

Also, although description has been made in the above-described embodiment exemplifying the cartridge 20 that has a configuration where the cartridge seal 27 is peeled away from the nozzle cover 24, this is but one suitable example of the cartridge 20 that can be unsealed at the time of use. Alternatively, tearing the cartridge seal 27 to unseal, for example, is an example of a structure that can be unsealed. In a case of tearing to unseal, the tear is preferably around a size to where the medicine such as the powdered medicine M can be sufficiently ejected. Also, a structure may be made where the cartridge seal 27 is automatically torn and unsealed by an action at the time of attaching the cartridge 20 to the sprayer 30, such as pressing the opening 23a of the medicine container 21 against the edge (or some sort of protruding part or protruding portion, etc., omitted from illustration) of the cylindrical portion 31b of the sprayer 30, for example, or alternatively by an action of screwing the screw portion (or stepped portion) 23b of the cylindrical base portion 23 of the medicine container 21 to the screw portion 31d of the sprayer 30, or the like.

Also, although description has been made in the above-described embodiment regarding a configuration enabling the cartridge seal 27 to be unsealed at the time of use and the cartridge 20 to be attached to the sprayer 30 and used, this also is but one suitable example of the nasally-administrable medicine administering device 10, or the cartridge 20 and sprayer 30 configuring the same. Alternatively, an arrangement may be made where the nasally-administrable medicine administering device 10 is in a state where the cartridge 20 and sprayer 30 are assembled to begin with, for example (see FIG. 1 and FIG. 2, etc.). In such a case, various points that have been difficult with conventional devices, such as improved uniformity of amount administered in each dose, improved drug preservability in the nasally-administrable medicine administering device 10 serving as the preservation container, facilitating ease-of-use regarding administration operations, and improved portability, can be realized in the same way as the above-described embodiment.

Although the nasally-administrable medicine administering device 10 such as described above, or the cartridge 20 configuring the same, is suitable as a device to administer nasally-administrable medicine, the usage is not particularly restricted to this. For example, while nasal administration heretofore has primarily been local treatment mainly to treat rhinitis, as of recent there have been many nasally-administrable medicines brought to market that aim for nasal mucosal absorption of drugs regarding which systemic action can be anticipated, such as drugs that alleviate migraine headaches and carcinomatous pain, and uses of the nasally-administrable medicine administering device 10 also include these. Also, research is being undertaken to deliver drugs to the brain from the olfactory region in the nasal cavities, and uses of the nasally-administrable medicine administering device 10 also include arrangements where nasally-administrable medicine is delivered to the olfactory region in the nasal cavities. Further, in pharmaceutical development, there is active development of biopharmaceuticals which require strict control of administration amount and strict preservation management. Demand for nasal-administration applications of such pharmaceuticals is also increasing, and such usages are also included.

Other specific examples other than administering nasally-administer medicine include such as listed below.

A cartridge used for managing physiologically active substances such as low-molecular compounds, peptide drugs, vaccines, nucleic acids, proteins, antibodies, and so forth.

A nasally-administrable medicine administering device (powdered medicine dispensing device for nasal cavities) used for administering physiologically active substances such as low-molecular compounds, peptide drugs, vaccines, nucleic acids, proteins, and so forth.

A nasally-administrable medicine administering device (powdered medicine dispensing device for nasal cavities) used for local action regarding rhinitis, sinus inflammation, and so forth.

A nasally-administrable medicine administering device (powdered medicine dispensing device for nasal cavities) used for absorption of nasal mucosal absorption of drugs regarding which systemic action can be anticipated.

A nasally-administrable medicine administering device (powdered medicine dispensing device for nasal cavities) used for mucosal immunological effects.

A nasally-administrable medicine administering device (powdered medicine dispensing device for nasal cavities) used for brain migration of drugs from the olfactory region in the nasal cavities.

INDUSTRIAL APPLICABILITY

The present invention is suitable for application to a powdered medicine dispensing device for nasal cavities, and to a nozzled cartridge and sprayer which are components thereof

What is claimed is:

1. A nozzled cartridge for storing medicine, comprising:

a medicine container that is to be filled with a predetermined quantity of a powdered medicine;

a nozzle portion that is formed on the medicine container and that ejects the powdered medicine;

a nozzle cover that closes an opening in the nozzle portion; and a plug to close another opening in the medicine container, and that is opened when administering medicine;

a nozzle base that is mounted to the other opening;

a retaining groove formed in the nozzle base so as to retain the plug;

a retaining edge portion formed on the plug so as to retain the retaining edge portion at the retaining groove;

a shaft portion formed on the plug, the shaft portion continuing to the retaining edge portion;

a stopper portion that is disposed on the shaft portion at a position spaced from the retaining edge portion and that has a shape that is to be hooked to a predetermined position of the nozzle base;

a tapered portion that is formed between the shaft portion and the retaining edge portion; and a seat formed on the nozzle base as a region that part of the plug abuts when the plug returns from the other opening, wherein the nozzled cartridge is detachably mountable to a sprayer when administering medicine, and wherein the powdered medicine is maintained in the nozzle portion by the plug, and wherein the plug is configured not to return into the retaining groove of the nozzle base once the retaining edge portion of the plug exits the retaining groove of the nozzle base.

2. The nozzled cartridge for storing medicine according to claim 1, wherein an unsealable cartridge seal is applied to an opening of the nozzle cover.

3. The nozzled cartridge for storing medicine according to claim 1, wherein the retaining groove that retains the plug is formed at the other opening of the medicine container.

4. The nozzled cartridge for storing medicine according to claim 3, wherein the retaining edge portion is formed on the plug, for retention at the retaining edge portion.

5. The nozzled cartridge for storing medicine according to claim 4, wherein the shaft portion continuing to the retaining edge portion, and a stopper portion that is disposed on the shaft portion at a position spaced from the retaining edge portion and that has a shape that is to be hooked to a predetermined position of the other opening, are formed on the plug.

6. The nozzled cartridge for storing medicine according to claim 5, wherein an air passageway that allows passage of air is formed on the stopper portion.

7. The nozzled cartridge for storing medicine according to claim 4, wherein a pointed portion that is pointed in shape from the retaining edge portion toward the opening of the nozzle portion is formed on the plug.

8. The nozzled cartridge for storing medicine according to claim 5, wherein the tapered portion is formed between the retaining edge portion of the plug and the shaft portion so as to have a diameter increasing from the shaft portion toward the retaining edge portion.

9. The nozzled cartridge for storing medicine according to claim 8, wherein the seat on which the plug or the tapered portion thereof abut after closing the other opening is formed at the other opening of the medicine container.

10. The nozzled cartridge for storing medicine according to claim 9, wherein the seat is formed to have a shape with which the plug or the tapered portion thereof comes into planar contact.

11. A sprayer that, in a state where the cartridge according to claim 1 is attached, feeds air into the cartridge and sprays the powdered medicine, the sprayer comprising:

a pump that feeds air into the cartridge; and a rod that is a member performing stroke movement in conjunction with movement of the pump, and that directly or indirectly abuts on the plug at a predetermined position partway along the stroke and opens the plug.

12. The sprayer according to claim 11, wherein a finger rest enabling a user to rest a finger when using the sprayer is provided on the sprayer.

13. The sprayer according to claim 12, wherein a venthole is formed in the rod.

14. The sprayer according to claim 13, wherein an aperture end of the venthole is formed at an end face of the rod.

15. The sprayer according to claim 11, wherein the pump includes a bellows pump.

16. The sprayer according to claim 11, wherein the pump includes a cylinder and a plunger.

* * * * *